(12) United States Patent
Brown

(10) Patent No.: US 8,527,206 B2
(45) Date of Patent: Sep. 3, 2013

(54) RESEARCH DATA COLLECTION AND ANALYSIS

(75) Inventor: Stephen J. Brown, Woodside, CA (US)

(73) Assignee: Robert Bosch GmbH, Stuttgart (DE)

( * ) Notice: Subject to any disclaimer, the term of this patent is extended or adjusted under 35 U.S.C. 154(b) by 305 days.

(21) Appl. No.: 10/741,168

(22) Filed: Dec. 18, 2003

(65) Prior Publication Data

US 2004/0193377 A1     Sep. 30, 2004

Related U.S. Application Data

(63) Continuation of application No. 09/799,852, filed on Mar. 5, 2001, now abandoned, which is a continuation-in-part of application No. 09/274,431, filed on Mar. 22, 1999, now Pat. No. 6,196,970.

(51) Int. Cl.
*G06F 19/00* (2011.01)
*A61B 5/00* (2006.01)

(52) U.S. Cl.
USPC ............................................ 702/19; 600/300

(58) Field of Classification Search
USPC ........................................................ 702/19
See application file for complete search history.

(56) References Cited

U.S. PATENT DOCUMENTS

| | | |
|---|---|---|
| 3,426,150 A | 2/1969 | Tygart |
| 3,566,365 A | 2/1971 | Rawson et al. |
| 3,566,370 A | 2/1971 | Worthington, Jr. et al. |
| 3,768,014 A | 10/1973 | Smith |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,417,306 A | 11/1983 | Citron et al. |
| 4,422,081 A | 12/1983 | Woods et al. |
| 4,449,536 A | 5/1984 | Weaver |
| 4,465,077 A | 8/1984 | Schneider |
| 4,473,884 A | 9/1984 | Behl |
| 4,519,398 A | 5/1985 | Lisiecki et al. |
| 4,531,527 A | 7/1985 | Reinhold, Jr. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,685,059 A | 8/1987 | Yamamoto |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,731,726 A | 3/1988 | Allen, III |
| 4,768,229 A | 8/1988 | Benjamin et al. |
| 4,779,199 A | 10/1988 | Yoneda et al. |
| 4,782,511 A | 11/1988 | Nemec et al. |
| 4,796,639 A | 1/1989 | Snow et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,858,354 A | 8/1989 | Gettler |
| 4,858,617 A | 8/1989 | Sanders |
| 4,890,621 A | 1/1990 | Hakky |
| 4,897,869 A | 1/1990 | Takahashi |
| 4,907,973 A | 3/1990 | Hon |
| 4,933,873 A | 6/1990 | Kaufman et al. |
| 4,950,246 A | 8/1990 | Muller |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,979,509 A | 12/1990 | Hakky |
| 5,007,429 A | 4/1991 | Treatch et al. |

(Continued)

FOREIGN PATENT DOCUMENTS

| | | |
|---|---|---|
| EP | 0251520 | 7/1988 |
| EP | 0286456 | 10/1988 |

(Continued)

OTHER PUBLICATIONS

"+5V Powered Isolated RS-232 Drivers/Receivers" Maxim Integrated Products, "Blood Glucose Monitors", *Portable Health Device*, (1988),vol. 17(9), pp. 253-271.

(Continued)

*Primary Examiner* — John S Brusca
(74) *Attorney, Agent, or Firm* — Maginot, Moore & Beck

(57) ABSTRACT

The invention provides a method and system by which research data can be collected and analyzed during the course of the research testing, and the research testing itself possibly modified to account for conclusions drawn from the research data. In a first aspect of the invention, a research subject can respond to a protocol stored on a server by manipulating input keys on a remotely located client device onto which a research protocol has been installed. The protocol can include questions concerning the subject's physical or mental well being such as whether their symptoms are relieved or not, or even exacerbated. The protocol can also include calling for data obtained by coupling the client device with another medical device such as a glucose monitor.

18 Claims, 3 Drawing Sheets

(56) References Cited

U.S. PATENT DOCUMENTS

| | | | |
|---|---|---|---|
| 5,016,172 A | 5/1991 | Dessertine | |
| 5,019,974 A | 5/1991 | Beckers | |
| 5,024,225 A | 6/1991 | Fang | |
| 5,025,374 A | 6/1991 | Roizen et al. | |
| 5,034,807 A | 7/1991 | Von Kohorn | |
| 5,036,462 A | 7/1991 | Kaufman et al. | |
| 5,049,487 A | 9/1991 | Phillips et al. | |
| 5,050,612 A | 9/1991 | Matsumura | |
| 5,056,059 A | 10/1991 | Tivig et al. | |
| 5,059,394 A | 10/1991 | Phillips et al. | |
| 5,065,315 A | 11/1991 | Garcia | |
| 5,068,536 A | 11/1991 | Rosenthal | |
| 5,074,317 A | 12/1991 | Bondell et al. | |
| 5,077,476 A | 12/1991 | Rosenthal | |
| 5,095,798 A | 3/1992 | Okada et al. | |
| 5,109,414 A | 4/1992 | Harvey et al. | |
| 5,109,974 A | 5/1992 | Beer et al. | |
| 5,111,396 A | 5/1992 | Mills et al. | |
| 5,111,817 A | 5/1992 | Clark et al. | |
| 5,111,818 A | 5/1992 | Suzuki et al. | |
| 5,120,230 A | 6/1992 | Clark et al. | |
| 5,120,421 A | 6/1992 | Glass et al. | |
| 5,128,752 A | 7/1992 | Von Kohorn | |
| 5,134,391 A | 7/1992 | Okada | |
| 5,142,358 A | 8/1992 | Jason | |
| 5,142,484 A | 8/1992 | Kaufman et al. | |
| 5,176,502 A | 1/1993 | Sanderson et al. | |
| 5,182,707 A | 1/1993 | Cooper et al. | |
| 5,204,670 A | 4/1993 | Stinton | |
| 5,222,020 A | 6/1993 | Takeda | |
| 5,227,874 A | 7/1993 | Von Kohorn | |
| 5,228,450 A | 7/1993 | Sellers | |
| 5,231,990 A | 8/1993 | Gauglitz | |
| 5,249,044 A | 9/1993 | Von Kohorn | |
| 5,251,126 A | 10/1993 | Kahn et al. | |
| 5,261,401 A | 11/1993 | Baker et al. | |
| 5,262,943 A | 11/1993 | Thibado et al. | |
| 5,265,888 A | 11/1993 | Yamamoto et al. | |
| 5,266,179 A | 11/1993 | Nankai et al. | |
| 5,275,159 A | 1/1994 | Griebel | |
| 5,282,950 A | 2/1994 | Dietze | |
| 5,299,121 A | 3/1994 | Brill et al. | |
| 5,301,105 A | 4/1994 | Cummings, Jr. | |
| 5,304,468 A | 4/1994 | Phillips | |
| 5,307,263 A | 4/1994 | Brown | |
| 5,309,919 A | 5/1994 | Snell et al. | |
| 5,329,459 A | 7/1994 | Kaufman et al. | |
| 5,329,608 A | 7/1994 | Bocchiere et al. | |
| 5,331,549 A | 7/1994 | Crawford, Jr. | |
| 5,339,821 A | 8/1994 | Fujimoto | |
| 5,341,291 A | 8/1994 | Roizen et al. | |
| 5,343,239 A | 8/1994 | Lappington et al. | |
| 5,344,324 A | 9/1994 | O'Donnell et al. | |
| 5,357,427 A | 10/1994 | Langen et al. | |
| 5,366,896 A | 11/1994 | Margrey et al. | |
| 5,371,687 A | 12/1994 | Holmes, II et al. | |
| 5,375,604 A | 12/1994 | Kelly et al. | |
| 5,377,100 A | 12/1994 | Pope et al. | |
| 5,390,238 A | 2/1995 | Kirk et al. | |
| 5,399,821 A | 3/1995 | Inagaki et al. | |
| 5,410,471 A | 4/1995 | Alyfuku et al. | |
| 5,410,474 A | 4/1995 | Fox | |
| 5,429,140 A | 7/1995 | Burdea et al. | |
| 5,431,691 A | 7/1995 | Snell et al. | |
| 5,434,611 A | 7/1995 | Tamura | |
| 5,438,607 A | 8/1995 | Przygoda, Jr. et al. | |
| 5,441,047 A | 8/1995 | David et al. | |
| 5,454,721 A | 10/1995 | Kuch | |
| 5,454,722 A | 10/1995 | Holland et al. | |
| 5,456,606 A | 10/1995 | McIntyre | |
| 5,456,692 A | 10/1995 | Smith, Jr. et al. | |
| 5,458,123 A | 10/1995 | Unger | |
| 5,467,269 A | 11/1995 | Flaten | |
| 5,471,039 A | 11/1995 | Irwin, Jr. et al. | |
| 5,483,276 A | 1/1996 | Brooks et al. | |
| 5,488,412 A | 1/1996 | Majeti et al. | |
| 5,488,423 A | 1/1996 | Walkingshaw et al. | |
| 5,501,231 A | 3/1996 | Kaish | |
| 5,502,636 A | 3/1996 | Clarke | |
| 5,502,726 A | 3/1996 | Fischer | |
| 5,504,519 A | 4/1996 | Remillard | |
| 5,517,405 A | 5/1996 | McAndrew et al. | |
| 5,518,001 A | 5/1996 | Snell | |
| 5,519,433 A | 5/1996 | Lappington et al. | |
| 5,544,649 A | 8/1996 | David et al. | |
| 5,546,943 A | 8/1996 | Gould | |
| 5,549,117 A | 8/1996 | Tacklind et al. | |
| 5,550,575 A | 8/1996 | West et al. | |
| 5,553,609 A | 9/1996 | Chen | |
| 5,558,638 A | 9/1996 | Evers et al. | |
| 5,564,429 A | 10/1996 | Bornn et al. | |
| 5,569,212 A | 10/1996 | Brown | |
| 5,572,421 A | 11/1996 | Altman et al. | |
| 5,574,828 A | 11/1996 | Hayward et al. | |
| 5,576,952 A | 11/1996 | Stutman et al. | |
| 5,590,648 A | 1/1997 | Mitchell et al. | |
| 5,596,994 A | 1/1997 | Bro | |
| 5,597,307 A | 1/1997 | Redford et al. | |
| 5,601,435 A | 2/1997 | Quy | |
| 5,613,495 A | 3/1997 | Mills et al. | |
| 5,619,991 A | 4/1997 | Sloane | |
| 5,624,265 A | 4/1997 | Redford et al. | |
| 5,628,309 A | 5/1997 | Brown | |
| 5,629,981 A | 5/1997 | Nerlikar | |
| 5,631,844 A | 5/1997 | Magrey et al. | |
| 5,633,910 A | 5/1997 | Cohen | |
| 5,639,471 A | 6/1997 | Chait et al. | |
| 5,640,953 A | 6/1997 | Bishop et al. | |
| 5,642,731 A | 7/1997 | Kehr | |
| 5,642,936 A | 7/1997 | Evans | |
| 5,666,487 A | 9/1997 | Goodman et al. | |
| 5,670,711 A | 9/1997 | Detournay et al. | |
| 5,675,635 A | 10/1997 | Vos et al. | |
| 5,678,562 A | 10/1997 | Sellers | |
| 5,678,571 A | 10/1997 | Brown | |
| 5,687,322 A | 11/1997 | Deaton et al. | |
| 5,687,717 A | 11/1997 | Halpern et al. | |
| 5,687,734 A | 11/1997 | Dempsey et al. | |
| 5,704,364 A | 1/1998 | Saltzstein et al. | |
| 5,704,366 A | 1/1998 | Tacklind et al. | |
| 5,704,902 A | 1/1998 | Vandenbelt et al. | |
| 5,711,297 A | 1/1998 | Iliff | |
| 5,715,451 A | 2/1998 | Marlin | |
| 5,715,823 A | 2/1998 | Wood et al. | |
| 5,717,913 A | 2/1998 | Driscoll | |
| 5,720,733 A | 2/1998 | Brown | |
| 5,722,418 A | 3/1998 | Bro | |
| 5,727,153 A | 3/1998 | Powell | |
| 5,730,124 A | 3/1998 | Yamauchi | |
| 5,732,696 A | 3/1998 | Rapoport et al. | |
| 5,732,709 A | 3/1998 | Tacklind et al. | |
| 5,734,413 A | 3/1998 | Lappington et al. | |
| 5,752,234 A | 5/1998 | Withers | |
| 5,760,771 A | 6/1998 | Blonder et al. | |
| 5,772,585 A | 6/1998 | Lavin et al. | |
| 5,778,882 A | 7/1998 | Raymond et al. | |
| 5,782,814 A | 7/1998 | Brown et al. | |
| 5,785,650 A | 7/1998 | Akasaka et al. | |
| 5,791,342 A | 8/1998 | Woodard | |
| 5,792,117 A | 8/1998 | Brown | |
| 5,793,969 A | 8/1998 | Kamentsky et al. | |
| 5,796,393 A | 8/1998 | MacNaughton | |
| 5,802,494 A | 9/1998 | Kuno | |
| 5,810,747 A | 9/1998 | Brudny et al. | |
| 5,819,735 A | 10/1998 | Mansfield et al. | |
| 5,822,544 A | 10/1998 | Chaco et al. | |
| 5,825,283 A | 10/1998 | Camhi | |
| 5,827,180 A | 10/1998 | Goodman | |
| 5,828,943 A | 10/1998 | Brown | |
| 5,835,896 A | 11/1998 | Fisher et al. | |
| 5,868,669 A | 2/1999 | Iliff | |
| 5,875,432 A | 2/1999 | Sehr | |
| 5,879,163 A | 3/1999 | Brown et al. | |
| 5,893,077 A | 4/1999 | Griffin | |

| | | | |
|---|---|---|---|
| 5,893,098 A | 4/1999 | Peters et al. | |
| 5,897,493 A | 4/1999 | Brown | |
| 5,899,855 A | 5/1999 | Brown | |
| 5,911,687 A | 6/1999 | Sato et al. | |
| 5,913,310 A | 6/1999 | Brown | |
| 5,918,603 A | 7/1999 | Brown | |
| 5,920,477 A | 7/1999 | Hofbert et al. | |
| 5,933,136 A | 8/1999 | Brown | |
| 5,935,060 A | 8/1999 | Iliff | |
| 5,941,829 A | 8/1999 | Saltzstein et al. | |
| 5,961,446 A | 10/1999 | Beller et al. | |
| 5,978,466 A * | 11/1999 | Quattrocchi | 379/265.01 |
| 5,983,217 A | 11/1999 | Khosravi-Sichani et al. | |
| 5,987,471 A | 11/1999 | Bodine et al. | |
| 5,995,969 A | 11/1999 | Lee et al. | |
| 5,997,476 A | 12/1999 | Brown | |
| 6,001,065 A | 12/1999 | DeVito | |
| 6,022,315 A | 2/2000 | Iliff | |
| 6,022,615 A | 2/2000 | Rettenbacher | |
| 6,029,138 A | 2/2000 | Khorasani et al. | |
| 6,035,328 A | 3/2000 | Soukal | |
| 6,046,761 A | 4/2000 | Echerer | |
| 6,049,794 A | 4/2000 | Jacobs et al. | |
| 6,050,940 A | 4/2000 | Braun et al. | |
| 6,055,314 A | 4/2000 | Spies et al. | |
| 6,055,487 A | 4/2000 | Margery et al. | |
| 6,055,506 A | 4/2000 | Frasca, Jr. | |
| 6,057,758 A | 5/2000 | Dempsey et al. | |
| 6,110,148 A | 8/2000 | Brown et al. | |
| 6,138,145 A | 10/2000 | Kawanaka | |
| 6,151,586 A | 11/2000 | Brown | |
| 6,168,563 B1 | 1/2001 | Brown | |
| 6,177,940 B1 | 1/2001 | Bond et al. | |
| 6,189,029 B1 | 2/2001 | Fuerst | |
| 6,196,970 B1 | 3/2001 | Brown | |
| 6,221,012 B1 | 4/2001 | Maschke et al. | |
| 6,230,142 B1 * | 5/2001 | Benigno et al. | 705/3 |
| 6,248,065 B1 | 6/2001 | Brown | |
| 6,272,468 B1 | 8/2001 | Melrose | |
| 6,329,139 B1 * | 12/2001 | Nova et al. | 435/6 |
| 6,368,273 B1 | 4/2002 | Brown | |
| 7,353,238 B1 * | 4/2008 | Gliklich | 1/1 |
| 2002/0004798 A1 * | 1/2002 | Babula et al. | 707/104.1 |

FOREIGN PATENT DOCUMENTS

| | | |
|---|---|---|
| EP | 0320749 | 2/1989 |
| EP | 370599 | 5/1990 |
| EP | 0461910 | 12/1991 |
| EP | 508912 | 10/1992 |
| EP | 526166 | 2/1993 |
| EP | 0653718 | 11/1994 |
| EP | 676709 | 10/1995 |
| EP | 680727 | 11/1995 |
| EP | 761160 | 3/1997 |
| GB | 2218831 | 11/1989 |
| GB | 2225637 | 6/1990 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9529447 | 11/1995 |
| WO | WO-96/07908 | 3/1996 |
| WO | WO-96/25877 | 8/1996 |
| WO | WO-97/08605 | 3/1997 |
| WO | WO-97/12544 | 4/1997 |
| WO | WO-98/16895 | 4/1998 |

OTHER PUBLICATIONS

"Central Fetal Monitoring Systems ewith Optical Disk Storage", *New Technology Brief*, (Nov./Dec. 1988), vol. 2, No. 6, pp. 249-251.
"European Search Report", From 6858P005EP,(Mar. 27, 1998).
"How Flash Memory Works", *Internet printout of URL address*: http://www.howstuffworks.com/flash-memory4.htm, (Sep. 28, 2002),2 pages.
"Introducing the Next Generation of About Your Diabetes", *U.S. Pharmacopical Convention and American Diabetes Association*, (1993).
"The description of the Tandy Radio Shack TRS-80 Model 100/102 device available at http://www.old-computers.com/museum/computer.asp?c=233", *World Wide Web*, (Feb. 13, 2004),1-3.
Albisser, A. M., "Intelligent Instrumentation in Diabetic Management", *CRC Critical Reviews in Biomedical Engineering*, vol. 17, No. 1, pp. 1-24.
Anonymous, "Health Hero netowrk, inc. Receives First-Ever FDA Clearance for Connecting Medical Devices to Internet", *PR Newswire*, (Dec. 2, 1999),3 pages.
Billiard, A., et al., "Telematic Transmission of Computerized Blood Glucose Profiles for IDDM Patients", *Diabetes Care*, (Feb. 1991), vol. 14, No. 2, pp. 130-134.
Bower, "Brain Clues to Energy-efficient Learning", *Science News*, (Apr. 1992),v 141; p. 215(1); Dialog: File 647, Acct #1213949.
Bruce, "Health Hero Network CEO, CNNfn", *Digital Jam*, (Dec. 1, 1999),3 pages.
Bruce, et al., "The Effects of Sympathetic Nervous System Activation and Psychological Stress . . ", *Diabetologia*, (1992),.;; 35 (9); 835-843; Dialog: File 5, Acc#9629427.
Brunetti, P. , "A Simulation Study on a Self-Tuning Portable Controller of Blood Glucose", *The International Journal of Artifical Organs*, (1993), vol. 16, No. 16, pp. 51-57.
Caprihan, A. , et al., "A Simple Microcomputer for Biomedical Signal Processing", *IECI '78 Annual Conference Proceedings on Industrial Applications of Microprocessors*, (Mar. 20, 1978), 18-23.
Cheng, Joe H., "PCT Search Report", (Jan. 11, 1996).
Douglas, A. S., et al., "Hand-Held Glucose Monitor and Recorder", *Proceedings of the Annual International Conference of the IEEE Engineering in Medicine and Biology Society*, New Orleans, LA,(Nov. 1988),pp. 747-748.
Fabietti, P. G., et al., "Wearable System for Acquisition, Processing and Storage of the Signal from Amperometric Glucose Sensors", *The International Journal of Artificial Organs*, (1991), vol. 14, No. 3, pp. 175-178.
Finston, "Parent + Teacher = Healthy Child", *Diabetes Forecast*, (Apr. 1994),v47 n9; p. 26(5); Dialog: file 149, Acc# 15804228.
Fox, "Not My Type: Type B Behavior, Type I Diabetes Plus Stree Equals Blood Sugar Blues", *Health*, (Mar. 1988),v20 n3; pp. 22(1); Dialog: File 149, Acc#06397959.
Frieberger, Paul , "Video Game Takes on Diabetes Superhero "Captain Novolin" Offer Treatment Tips", *San Francisco Examiner*, (Jun. 26, 1992),Fourth Edition, Business Section B1.
Giuffrida, Antonio , et al., "Should We Pay the Patient?Review of Financial Incentives to enhance Patient compliance", *Biomedical Journal*, (1997), vol. 315, pp. 703-707.
Hauben, Jay R., "A Brief History of the Cleveland Free-Net", available at http://www.ais.org/~irh/acn7-1.a09.html, (1995), pp. 1-4.
Hauser, Thomas , et al., "Will Computers Replace or Complement the Diabetes Educator?", *The Medical Journal of Australia*, (Oct. 5, 1992), vol. 157, 489-491.
Horio, Hiroyuki , et al., "Clinical Telecommunication Network System for Home Monitoring", *Medical & Biological Engineering & Computing*, (Mar. 1994), vol. 32, 227-230.
Hunter, "Technological Advances in Bedside Monitoring: Biosensors", *Archives and Laboratory Medicine*, (Jul. 1987),pp. 633-636.
Kauffmann, Francine , et al., "Epidermiological Study of the Genetics and Environment of Asthma, Bronchial Hyperresponsiveness and Atopy", *Am. J. Respir. Crit. Care Med.*, (1997), vol. 156, pp. S123-S129.
Kaufman, Steven , "B., The Learning Game", *Nation's Business*, (Nov. 1993).
Kuykendall, V G., et al., "Assessment of Self-Monitored Blood Glucose results Using a Reflectance Meter with Memory and Microcomputer", *Symposium on Computer Applications in Medical Care*, (Jan. 1981), vol. 70, pp. 98-102.
Lacyk, John , "PCT Search Report", (Jun. 12, 1997).
Latman, N. S., "Evaluation of Electronic, Digital Blood Glucose Monitors", *Biomedical Instrumentation and Technology*, (1991), vol. 25, No. 1, 43-49.

Laughton, Miles E., "A Portable Microcomputer for Long-Term Physiological Monitoring in the Home and Work Environment", *Medical Monitoring in the Home and Work Environment*, (1990), pp. 47-57.

Leyerle, Beverly J., et al., "The PDMS as a Focal Point for Distributed Patient Data", *International Journal of Clinical Monitoring and Computing*, (1988), vol. 5, pp. 155-161.

Makikawa, M., et al., "Microprocessor-Based Memory Device for Ambulatory Heart Rate and Physical Activity Recording", *Methods of Information in Medicine*, (1994), vol. 33, No. 1, pp. 94-96.

Marsh, David G., "Approaches Toward the Genetic Analysis of Complex Traits Asthma and Atopy", *Am. J. Respir.Crit.Care Med.*, (1997), vol. 156, pp. S-133-S138.

Martinez, Fernando D., "Complexities of the Genetics of Asthma", *Am. J. Respir. Crit. Care Med.*, (1997), vol. 156, pp. S117-S122.

Mazzola, et al., "Video Diabetes: A Teaching Tool for Children with Insulin-Dependent Diabetes", *Proceedings—7th Annual Symposium on Computer Applications in Medical Care; Washington, DC; Dialog:*, (Oct. 1983),File 8, Acc#01624462.

Meissner, et al., "Building an Integrated Clinical and Research Network", *Proceedings of the SPIE*, (Oct. 24, 1995), vol. 2618, p. 92 99.

Moore, "New Applications Break Through Storage Boundaries", *Computer Technology Review*, (Oct. 1999), vol. 19, No. 10, p. 1.

Pfeiffer, E. F., "The Glucose Sensor: The Missing Link in Diabetes Therapy", *Hormone and Metabolic Research*, (1990), vol. 24, Suppl., pp. 154-164.

Poitout, V., et al., "A Glucose Mointoring System for on Line Estimation in Man of Blood Glucose Concentration Using a Miniaturized Glucose Sensor Implanted in the Subcutaneous Tissue and a Wearable Control Unit", *Diabetologia*, (1993), vol. 36, pp. 658-663.

Potter, David, "Fundamentals of PC-Based Data Acquisition", *Sensors*, (Feb. 1994), pp. 12-20.

Reis, Howard, "Telemedicine: Transmitting Expertise to the Point of Care", Proceedings: *Toward an Electronic Patient Record*, (1997), pp. 248-256.

Roberts;, "Diabetes and Stress: A Type A Connection?", *Psychology Today*, (Jul. 1987),v. 21; pp. 22(1); Dialog: File 149, Acc#05038381.

Rose, V. L., et al., "Decentralized Testing for Prothrombin Time and Activated Partial Thromboplastin Time Using a Dry Chemistry of Portable Analyser", *Archives of Pathology and Laboratory Medicine*, (Jun. 1993), vol. 117, pp. 611-617.

Schenkels, P., "Supplementary European Search Report", Application No. EP 97 92 2716, (Mar. 11, 2002).

Schork, Nicholas J., "Genetics of Complex Disease", *Am. J. Respir. Crit. Care Med.*, (1997), vol. 156, pp. s103-S109.

Schrezenmeir, J., et al., "Computer Assisted Insulin Dosage Adjustment—Perspective for Diabetes Control", *Hormone and Metabolic Research, Supplement Series*, (1990), vol. 24, pp. 116-123.

Shandle, Jack, "Who Will dominate the desktop in the 90s?", *Electronics*, (Feb. 1990), pp. 48-50.

Shults, Marc C., et al., "A Telemetry-Instrumentation System for Monitoring Multiple Subcutaneously Implanted Glucose Sensors", *IEEE Transactions on Biomedical Engineering*, (Oct. 1994), vol. 41, No. 10, pp. 937-942.

Soeldner, J. S., "Treatment of Diabetes Mellitus by Devices", *The American Journal of Medicine*, Jan. 1981 ,vol. 70, 183-194.

Updike, Stuart J., et al., "Laboratory Evaluation of New Resusable Blood Glucose Sensor", *Diabetes Care*, (Nov./Dec. 1988), vol. 11, No. 10, pp. 801-807.

Vallera, D. A., et al., "Accuracy of Portable Blood Glucose Monitoring", *American Journal of Clinical Pathology*, (1991), vol. 95, No. 2, pp. 247-252.

Voelker, Rebecca, "Shoe Leather Therapy is Gaining on TB", *Jama*, (Mar. 13, 1996), vol. 275, 743.

Wyatt, J. C., "Clinical Data Systems, Part 2: Components and Techniques", *Lancet*, (Dec. 1994), vol. 344, No. 8937, pp. 1609-1614.

Yoshizawa, Daisuke, et al., "The Development of a Data Processing System with Personal Computer MSX Standard System for Flow Injection Analysis", *Journal of Flow Injection Analysis*, (1988), V. 5, No. 2. pp. 101-110.

\* cited by examiner

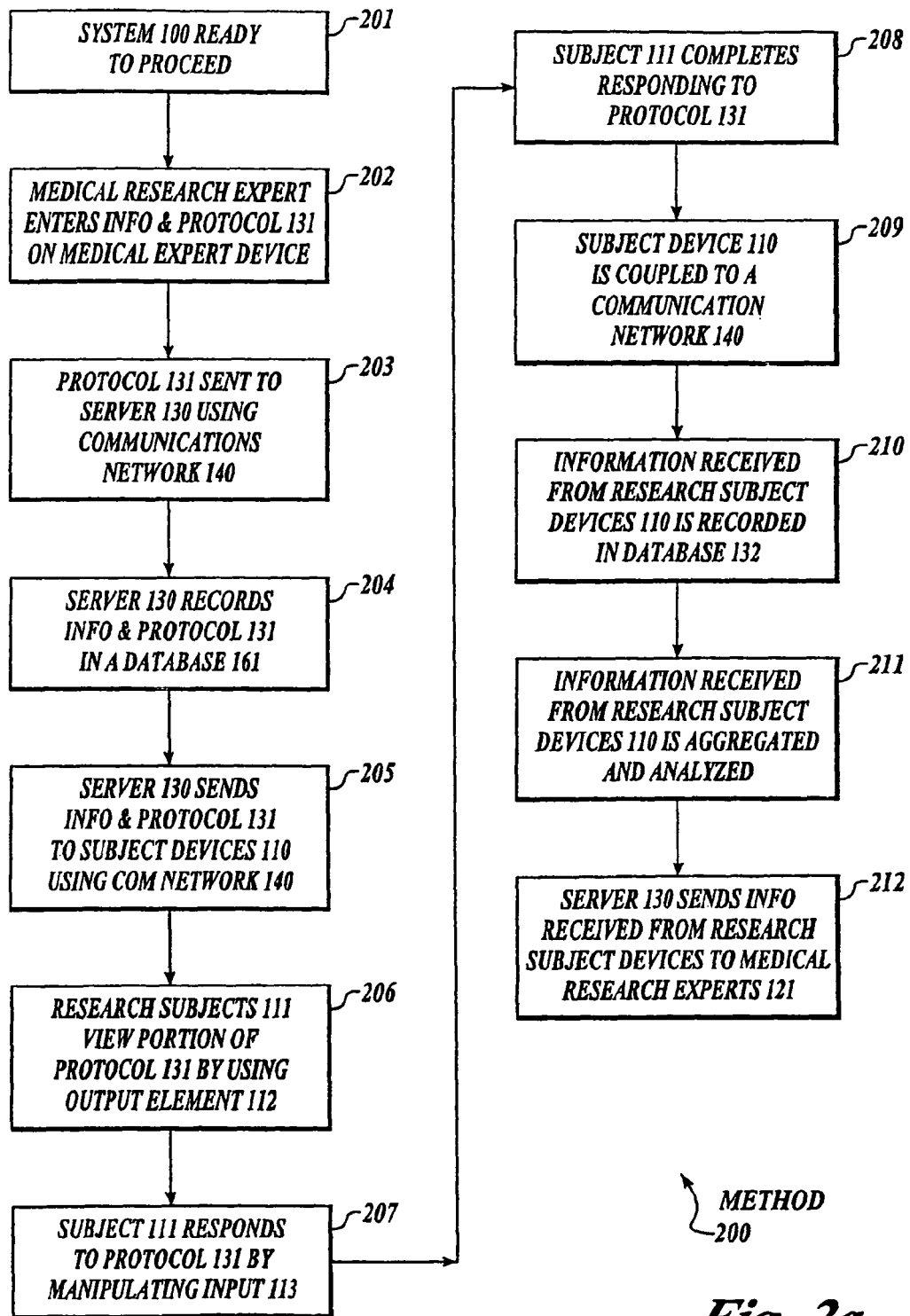

RESEARCH DATA COLLECTION AND ANALYSIS

RELATED APPLICATIONS

This application is a continuation of U.S. Ser. No. 09/799,852 filed Mar. 5, 2001 now abandoned, which is continuation-in-part of U.S. Ser. No. 09/274,431 filed Mar. 22, 1999, now U.S. Pat. No. 6,196,970.

Inventions described herein can be used in combination or conjunction with inventions described in the following patent application(s):

application Ser. No. 09/201,323, Express Mail Mailing No. EE143637591US, filed Nov. 30, 1998, in the name of Stephen J. Brown, titled "Leveraging Interaction with A Community of Individuals," assigned to the same assignee, and all pending cases claiming priority thereof.

application Ser. No. 09/274,433, Express Mail Mailing No. EJ384008769US, filed Mar. 22, 1999, in the name of Steven J. Brown, titled "Patient Initiated Contact," assigned to the same assignee, and all pending cases claiming priority thereof.

These applications are each hereby incorporated by reference as if fully set forth herein. These applications are collectively referred to herein as "incorporated disclosures."

BACKGROUND OF THE INVENTION

1. Field of the Invention

This invention relates to research data collection and analysis.

2. Related Art

Human beings are sometimes used as subjects in different types of medical, psychological, and other research. Generally, such research fits into one of several broad categories: academic or industrial research, FDA clinical trials, and marketing and sales research. Human beings are also used as research subjects in experiments designed to correlate genotype and phenotype with drug reactions. For example, a researcher may seek to learn whether patients with the genotype for sickle cell disorder experience greater light sensitivity when taking a specific antibiotic.

Academic and industrial investigators often employ human subjects to learn how humans respond to some pre-determined stimuli such as a drug or a psychological event. For a first example, an academic researcher may use post-menopausal women as subjects in experiments designed to widen our understanding of the neuroendocrine response to ethanol. Many different types of data can be obtained in such experiments. In this first example, a researcher could correlate the data on different hormone levels with blood alcohol levels, the frequency of selected patient behaviors, number of cigarettes smoked and many other possible factors. These data can be aggregated with similar data from other researchers and conclusions can be drawn based upon their observations.

A second area in which human subjects are sometimes used as a research tool involves government approval of new drugs for human patients. The Food and Drug Administration (FDA) approves new drugs that are to be marketed for human consumption. Presently, FDA approval is contingent upon the drug successfully passing three phases of testing during which the drug is blindly administered to human subjects. Taken together, these three phases of testing are called clinical trials. Only those drugs that successfully complete all three phases of clinical trials can be marketed.

In the general course of events, the sponsor of a drug will submit an application and protocol to the FDA for clinical testing. After the application is reviewed and approved, Phase I of clinical testing begins. Experienced clinical investigators administer the drug to a small number of healthy volunteers. Although drug dosage and metabolism may be studied, the main focus of this initial testing phase is drug safety. Since safety concerns are paramount, testing is preformed on a relatively small population (between 20 to 100 subjects) for a short period of time. Drugs that induce toxic reactions or other adverse effects do not advance to Phase II. This initial screening eliminates approximately 30% of all applicants.

The main focus of Phase II testing is to determine whether the drug is an effective treatment. Since the focus is on the effectiveness of the drug and the threat of adverse reactions has been largely ruled out, Phase II clinical trials involve a larger number of subjects (up to several hundred) who suffer from a problem the drug is designed to treat. Phase II trials may involve the blind testing of up to several hundred subjects. Only 33% of all drugs advance to phase III testing.

Phase III testing may involve up to several thousand subjects. This phase lasts longer (between one to four years) than either Phase I or Phase II. Here, the safety, dosage and effectiveness of the new drug are all rigorously screened. Between 25-30% of all drugs pass phase III trials and receive the required approval necessary for marketing.

An additional level of testing is also employed. After a new drug has passed all three phases of clinical trials, researchers may also want to learn if any adverse effects occur after the drug is marketed. Thus, additional investigation may involve post-marketing surveillance of patients who have been administered the drug after it is approved by the FDA. Such post marketing surveillance is a useful tool that helps researchers learn more about how patients respond to a specific drug.

Known marketing and sales research includes attempting to elicit responses from human participants regarding whether those participants would be more or less likely to purchase selected goods or services. It is known to attempt to correlate responses with demographic data about the participants (such as age, gender, household income, or residence locale), as well as psychological and other information about participants (such as whether participants are considered "early adopters").

Known methods for collecting and analyzing data from human subjects in research suffer from several drawbacks. While these methods generally achieve their respective goals of learning more about the human response to various stimuli, screening out ineffective and unnecessarily toxic drugs, and providing useful information for marketing or sales, known methods suffer from several drawbacks and limitations that can make them time-consuming or inefficient.

A first problem in the known art is that collection of data from subjects or participants in research-or clinical trials often involves obtaining and analyzing fuzzy assessments from subjects who are not necessarily under the continual observation of a clinician or other personnel. Indeed, many subjects (such as the controls in clinical trials) are not under the care of a physician at all, but merely report to an expert researcher periodically for testing and analysis. Such testing and analysis frequently involves self-reporting a number of parameters. A subject's answer to an inquiry often involves the making of a fuzzy assessment of physical state, mood or quality of life. Accordingly, there is a need for a method to evaluate and standardize such fuzzy self-assessments.

A second problem in the known art is that researchers are unable to respond to incoming data in real time. In known methods, data from research or clinical trials is collected and stored for analysis at a later time. Frequently, researchers or lab technicians enter their observations in a paper copy of a log book or lab notebook. Often these results are entered near the end of an experiment. This practice makes it impossible for an investigator to evaluate the data or change the experimental design. While researchers may have an approximate idea as to the general trend of incoming data, they are frequently unable to respond to that trend until the data is analyzed, well after any opportunity for altering the method of collection or the nature of the data collected. Accordingly, researchers are unable to modify a clinical protocol while in process. This inability to evaluate and respond to incoming data during data collection can create conditions that are dangerous for the subjects of the research. It is believed that morbidity and mortality associated with evaluation of new drugs would be substantially reduced if researchers could respond during the research, such as to halt the clinical trial or adjust the drug dosage. Accordingly, there is a need to evaluate and respond to subjects in real time.

A third problem in the known art is that collection of data from research and clinical trials often calls for the aggregation of data from many different geographical testing sites. It is believed that drug testing and other research would be quicker if there were a way to aggregate data and respond to it in real time, during the time of the trials or research. Accordingly, there is a need to aggregate and analyze data from many remote sites.

A fourth problem in the known art is that identification of subjects in clinical trials who respond to a drug is not always readily apparent because it frequently requires evaluation of many different parameters. Part of this problem involves the nature of disease. In some cases, an acute condition will spontaneously heal, regardless of treatment. Chronic diseases often follow an unpredictable course as symptoms abate for a time and then worsen. Under these conditions, it is often difficult to determine whether the change in the subject's condition may be attributed to the drug or some other factor. Identifying subjects who respond to a drug is particularly problematic in Phase II trials where the issue is the efficacy of the drug. Accordingly, there is a need to be able to distinguish responders from non-responders on the basis of many different factors.

A fifth problem in the known art involves the nature of research with human subjects. Most experiments involving administration of drugs are either blinded or double blinded. In blinded studies, the subject does not know whether they are receiving the active drug or a placebo. In essence, although the investigator knows what the subject is receiving, the subject does not know whether or not they are being used as a control. In double-blinded subjects, neither the researcher nor the research subject is aware of the subject's status. Blinded studies are problematic because researcher may impose his own bias on the incoming data. Double-blinded studies are problematic because the researcher may not be sensitive to phenomena that the subject is experiencing. Another problem raised in double-blinded studies is that the investigator very often becomes unblinded when observing the effect of a drug on a research subject. According, there is a need for an impartial, unbiased observer that remains responsive to the research subjects.

Accordingly, it would be advantageous to provide a technique by which research data can be collected and analyzed during the course of the research testing, and the research testing itself possibly modified to account for conclusions drawn from the research data. For example, it would be advantageous to provide a device that can be carried by a research subject or participant that can be coupled and uncoupled to a communication system that is also accessible to researchers and other remote experts. Such a device would allow researchers to (1) collect, analyze and respond to input from the research subjects or participants in real time, (2) evaluate fuzzy assessments made by a subject or participant by making progressively narrower inquiries designed to obtain specific data, (3) aggregate and analyze data from a large number of remote sites quickly, (4) change the research protocol in response to input from subjects in real time and (5) rapidly identify responders and non-responders by correlating the data with a number of disparate parameters that are not necessarily apparent when the study begins. These advantages are achieved in embodiments of the invention in which a research subject enters data using a client device that is coupled to a server via a communication link.

SUMMARY OF THE INVENTION

The invention provides a method and system by which research data can be collected and analyzed during the course of the research testing, and the research testing itself possibly modified to account for conclusions drawn from the research data. In a first aspect of the invention, a research subject can respond to a protocol stored on a server by manipulating input keys on a remotely located client device onto which a research protocol has been installed. The protocol can include questions concerning the subject's physical or mental well being such as whether their symptoms are relieved or not, or even exacerbated. The protocol can also include calling for data obtained by coupling the client device with another medical device such as a glucose monitor. In a preferred embodiment, the subject is presented with narrowly structured questions and suggested answers provided by the protocol. The set of possible answers is restricted. In the event that a suggested answer is ambiguous, inapplicable or raises new questions, a protocol can present a new question to the subject. This elimination of fuzzy answers imposes a logical structure upon the subjects' assessments.

In a second aspect of the invention, data entered by the subject is relayed using a communication link to a server device. This incoming data can be aggregated with other incoming data from subjects and their associated client devices. In a preferred embodiment, the data is statistically analyzed according to parameters set by the protocol.

In a third aspect of the invention, a remote expert research clinician can review incoming data from either the aggregated population or from individuals as it is being analyzed. Such rapid collection and analysis allows a researcher to change the protocol in response to the trend of the data, correlate different parameters of the data so as to better identify subjects that are responding to treatment and schedule appropriate interventions as needed. The researcher can also identify specific subgroups among the population of subjects, initiate new lines of inquiry and test new sub-hypotheses that may be raised by the incoming data. This includes correlating different drug responses experienced by phenotypically similar subjects with gene expression, and other variables.

DETAILED DESCRIPTION OF THE PREFERRED EMBODIMENT

In the following descriptions, a preferred embodiment of the invention is described with regard to preferred process steps and data structures. Embodiments of the invention can be implemented using general-purpose processors or special purpose processors operating under program control, or other circuits, adapted to particular process steps and data structures described herein. Implementation of the process steps and data structures described herein would not require undue experimentation or further invention.

SYSTEM ELEMENTS

Figure 1:
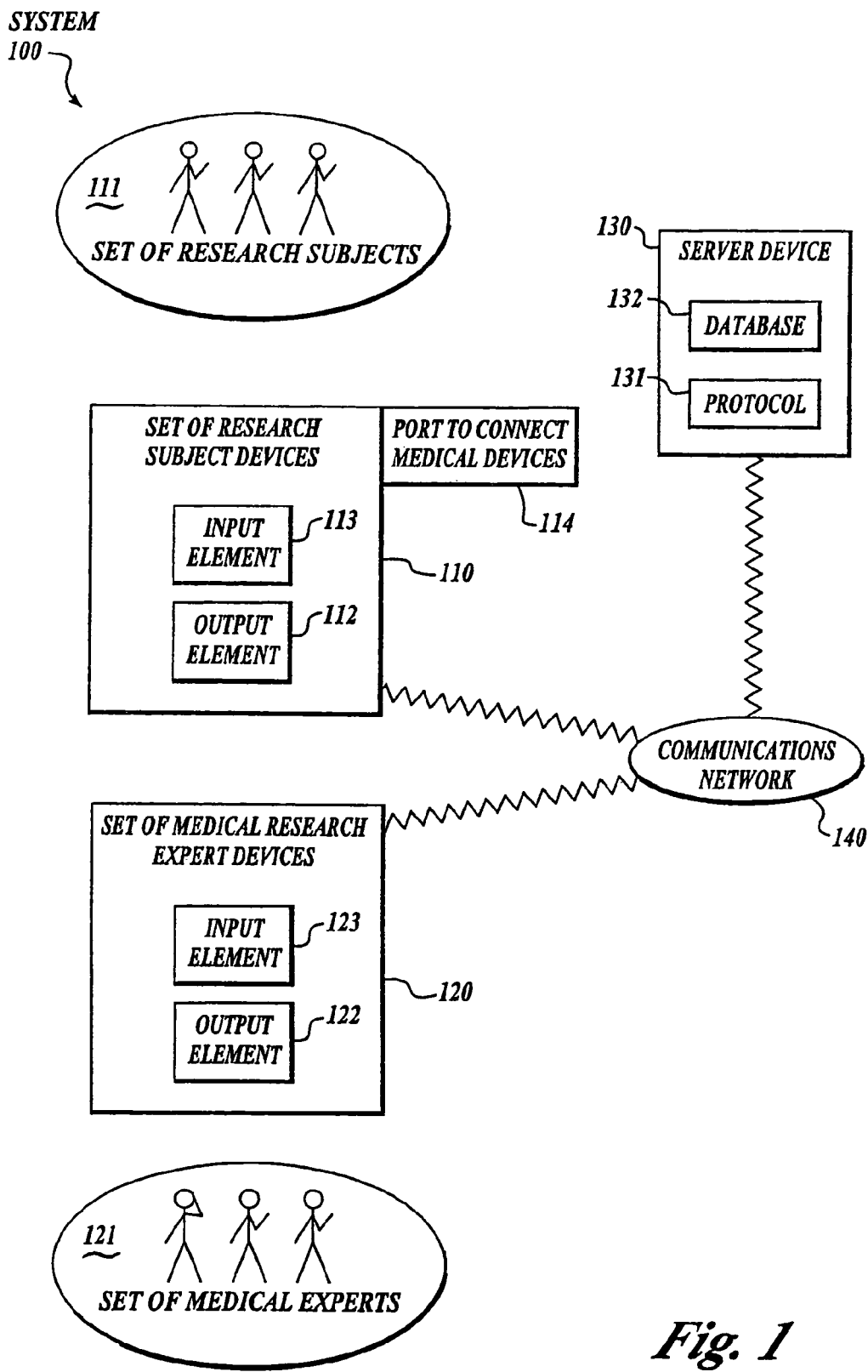
FIG. 1 shows a block diagram of a system 100 to collect and analyze data from human research subjects.

FIG. 1 shows a block diagram of a system 100 to collect and analyze data from human subjects engaged in medical research using a protocol or other intelligent message, which acts in place of a researcher, investigator, clinician or other medical expert.

A system 100 includes a set of subject devices 110, a set of medical research expert device 120 and a server device 130. The subject device 110, the medical research expert device 120 and the service device 130 are coupled using a communication network 140.

The set of research subject devices 110 is used by a set of research subjects 111. Each research subject device includes an output element 112, an input element 113 and a port 114. The subject 111 manipulates the subject device 110 to send feedback from the subject 111 to the server 130 and to receive information from the protocol 131. Port 114 can be coupled to a variety of medical appliances to send additional data to the server 130.

The set of medical research expert devices 120 is used by a set of medical research experts 121. Each medical expert device includes an output element 122 and an input element 123.

The server device 130 includes a protocol 131 and a database 132.

For further information regarding a data structure and simplified research subject interface, and preferred embodiments of the subject device 110, medical research expert device 120 and the server device 130 including data base 132, see related application Ser. No. 09/201,323, Express Mailing No. EE143637591US, filed Nov. 30, 1998 in the name of Stephen J. Brown, titled "Leveraging Interaction with a Community of Individuals," assigned to the same assignee, and other related applications incorporated by reference therein.

For further information regarding the protocol or other intelligent message used by the system, see related application Ser. No. 09/203,882, Express Mailing No. EE143637565US, filed Dec. 1, 1998, in the name of Stephen, J. Brown, titled "Remote User Data Collection Protocols Including Data Structures and User Interface," assigned to the same assignee, and other related applications incorporated by references therein.

For information regarding a medicine dispenser which can be used by the system, see related application Ser. No. 09/203,880, Express Mail Mailing No. EE143637557US, filed Dec. 1, 1998, in the name of Stephen J. Brown, et al., titled "Using a Computer Communication System with Feedback to Dispense Medicine," assigned to the same assignee, and other related applications incorporated by reference therein.

For information regarding genotype and phenotype correlation, see related application Ser. No. 08/850,840, Express Mail Mailing No. EI113824573US, filed May 3, 1998 in the name of Stephen J. Brown, et al. titled "System and Method for Preventing, Diagnosing and Treating Genetic and Pathogen-Caused Disease", assigned to the same assignee, and application Ser. No. 09/041,809, Express Mail Mailing No. EE262620680US, filed Mar. 13, 1998 in the name of Stephen J Brown, et al. titled Phenoscope and Phenobase", assigned to the same assignee.

Method of Operation

Figure 2B:
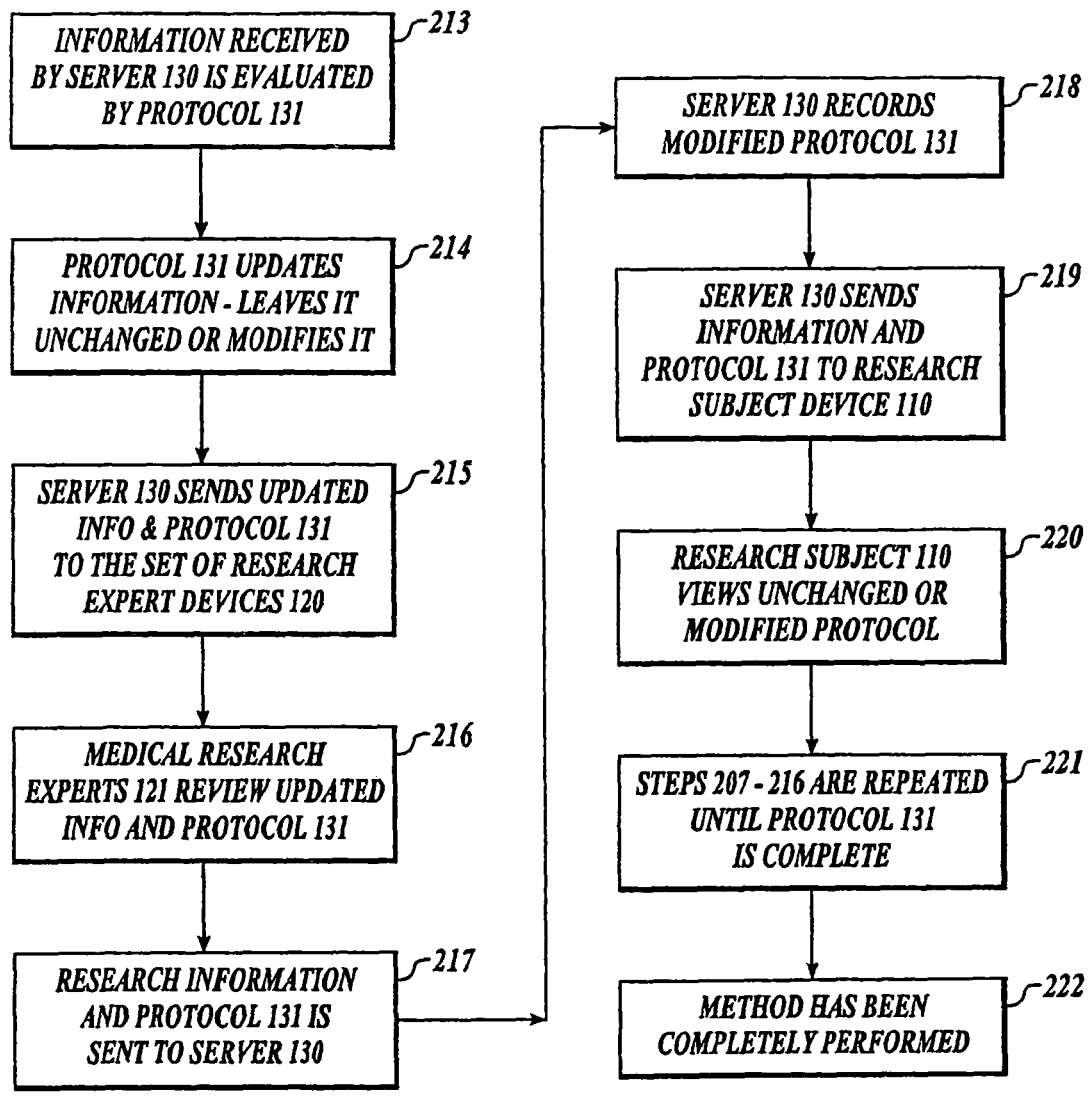
FIG. 2 shows a process flow diagram of a method for operating a system for interaction with a community of individuals, including research subjects and investigators.

FIG. 2 shows a process flow diagram of a method for collecting data from human research subjects to be performed by the system and for analyzing and reporting that data to research experts.

A method 200 is performed by a system 100, as follows:

At a flow point 201, the system 100 is ready to proceed.

At a step 202, a medical research expert 121 enters information concerning the type of data to be collected from a set of subjects 111 and a protocol 131 on a medical research expert device 120.

At a step 203, the research information and protocol 131 entered onto the medical research expert device 120 is sent to a server device 130 using the communication network 140.

At a step 204, the server device 130 records the research information and protocol 131 submitted by the medical research expert 121 in the database 132.

At a step 205 in a preferred embodiment, the server device 130 sends the research information and protocol 131 to a set of research subject devices 110 using the communication network 140. In alternative embodiments, the server device 130 may send the research and protocol 131 information to other medical research experts 121 for review.

At a step 206 the set of research subjects 111 view some portion of the protocol 131 that was sent to the set of research subject devices 110 by looking at a presentation screen or other output element 112 contained in the research subject device 110.

At a step 207, the set of subjects 111 respond to the protocol 131 sent to the set of research subject devices 110 by manipulating a keypad or other input 113 included in the research subject device 110. Alternatively, the set of subjects 111 respond to the protocol 131 sent to them by coupling the subject device 110, using a port 114 included in the research subject device 110, to a medical appliance such as one or more of, or some combination of, the following: a blood glucose meter, an oxymeter, a peak flow meter, a blood pressure gauge, a weight scale, a pulse sensor, a home infusion system, a CPAP sleep apnea device, a location sensing device, a digital video camera or a drug dispensing apparatus.

At a step 208, the research subject 111 has completed responding to the protocol 131.

At a step 209, the subject device 110 is coupled to a communication network 140 which sends the information entered by the subject 111 in response to the protocol 131 to the server device 130.

At a step 210 the information received by the server device 130 is recorded in the database 132.

At a step 211, the information received from the research subject devices 110 is aggregated and statistically analyzed.

At a step 212, in a preferred embodiment, the server device 130 sends the information received from the research subject devices 110 to the various medical research experts 121. In an alternative embodiment, the server device 130 does not send the information. The information remains available on the server device 130 where it can be looked up by interested parties.

At a step 213, the information received by the server device 130 from the research subject device 110 is evaluated by the protocol 131.

At a step 214, the protocol 131 updates the research information and either leaves it unchanged or modifies it in accordance with the protocol logic.

At a step 215, in a preferred embodiment, the server device 130 sends the updated research information and protocol 131 to the set of research expert devices 121 using the communication network 140. In an alternative embodiment, the server device 130 does not send the updated research information to the medical research expert device 120.

At a step 216, the medical research expert 121 review the updated information and protocol 131 and the other information input by the set of research subjects 111 and either leave the updated research information and protocol unchanged or modify it as necessary. In an alternative embodiment, step 216 does not take place.

At a step 217, in a preferred embodiment, the research information and protocol 131 as unchanged or modified by the medical research expert(s) 121 is sent to the server device 130 using the communications network 140. In an alternative embodiment, step 217 does not take place.

At a step 218, the server device 130 records the modified research and protocol 131 information sent by the medical research expert 121 in the database 132. In an alternative embodiment, step 218 does not take place.

At a step 219 in a preferred embodiment, the server device 130 sends the research and protocol 131 information as unchanged or as modified by the medical research expert 121 to the research subject device 110 using the communication network 130. In an alternative embodiment, step 219 does not take place.

At a step 220, the research subject 111 views the unchanged or modified protocol, as they did in step 206.

At a step 221, the method repeats steps 207 through 216 until all desired information is obtained from the subject and the protocol 131 has been completed. After sending the information to the medical research expert(s) for final review (step 216), the information resides in the database and the method is complete.

At a step 222, the method has completely performed a system 100.

Alternative Embodiments

Although preferred embodiments are disclosed herein, many variations are possible which remain within the concept, scope and spirit of the invention, and these variations would become clear to those skilled in the art after perusal of this application.

The invention claimed is:

1. A method comprising:
    (a) allowing one or more human subjects to manipulate an input device to provide one or more answers as data in response to one or more questions presented on a presentation screen, wherein said questions concern one or more of a physical well being, a mental well being, one or more symptoms, or one or more other psychological conditions of the one or more human subjects in accordance with a medical research protocol;
    (b) collecting data from said one or more human subjects according to said medical research protocol;
    (c) sending data collected from said input device to a server device relatively remote from said input device via a communication link;
    (d) performing a data manipulation technique on data associated with more than one of said subjects;
    (e) presenting a result of said data manipulation technique at a presentation device relatively remote from said server device; and
    (f) modifying said medical research protocol in response to said result, wherein
        the collection of data is altered for at least some performances thereof, and
        step (e) occurs in conjunction with repeatedly performing step (b).

2. The method as in claim 1, wherein each said subject is associated with an individual input device.

3. The method as in claim 1, wherein said data manipulation technique includes aggregating said data, combining said data, or performing a statistical operation with regard to said data.

4. The method as in claim 1, wherein said data manipulation technique includes:
    storing said data at a device relatively remote from said input device;
    receiving a data manipulation inquiry from said presentation device;
    performing said data manipulation inquiry; and
    presenting a result of said data manipulation inquiry at said presentation device.

5. The method as in claim 1, wherein said data manipulation technique is specified by at least one of said medical research protocol and said modified medical research protocol.

6. The method as in claim 1, wherein step (c) is performed in response to a time period, an event associated with said presentation device, or an event associated with said subject.

7. The method as in claim 1, wherein at least one of said medical research protocol and said modified medical research protocol includes presenting instructions to one said subject and receiving data from said input device in response thereto.

8. The method as in claim 7, wherein said input device includes a keyboard, a microphone, a motion sensor, a pointing device, a set of buttons, or a switch.

9. The method as in claim 7, wherein said input device includes a medical device.

10. The method as in claim 1, wherein at least one of said medical research protocol and said modified medical research protocol is performed at a client device located relatively proximate to said input device.

11. The method as in claim 10, wherein said medical research protocol is modified at said client device in response to said presentation device.

12. The method as in claim 10, further comprising modifying said medical research protocol with said server device.

13. The method as in claim 1, further comprising:
    providing a second medical research protocol;
    selecting a portion of said plurality of subjects in response to said data manipulation technique; and
    altering the collection of data to perform said one first medical research protocol for unselected ones of said subjects, and to perform said second medical research protocol for selected ones of said subjects;
    wherein the collection of data is altered for at least some performances thereof.

14. The method as in claim 13, wherein the selection of a portion of the human subject is performed in response to a genotype, a gene expression, or a phenotype of one or more of said subjects.

15. The method of claim 1, wherein the input device is portable.

16. The method according to claim 1, wherein step (a) further comprises the step of:

presenting narrowly structured questions with suggested answers via said input device to allow said one or more human subjects to select from any one of said suggested answers.

17. The method according to claim 16, further comprising the step of:

presenting a selected one of said suggested answers as data via said input device to said server device.

18. A method comprising:
(a) collecting data from a plurality of human subjects, the collection of data comprises the following substeps:
  (i) associating an input device with at least one subject, the input device comprising an input element and an output element;
  (ii) presenting questions formulated according to a medical research protocol to the associated subject via the output element of the input device on a presentation screen, wherein said questions concern one or more of a physical well being, a mental well being, one or more symptoms, or one or more other psychological conditions of the plurality of human subjects; and
  (iii) allowing the subject to manipulate the input element of the input device to provide answers as data in response to the questions;
(b) sending the collected data from the input device to a server device relatively remote from the input device via a communication link;
(c) performing a data manipulation technique on data associated with more than one of said subjects;
(d) presenting a result of said data manipulation technique at a presentation device remote from said input device; and
(e) modifying said protocol in response to said result, wherein the collection of data is altered for at least some performances thereof, and step (d) is performed in conjunction with repeatedly performing step (a).

* * * * *